United States Patent [19]

DesBois et al.

[11] Patent Number: 4,701,551
[45] Date of Patent: Oct. 20, 1987

[54] PROCESS FOR PREPARING TRIFLUOROACETIC OR TRICHLOROACETIC ACID ESTERS

[75] Inventors: Michel DesBois, Rillieux La Pape; Louis Amiet, Lyons, both of France

[73] Assignee: Rhone-Poulenc Specialites Chimiques, Courbevoie, France

[21] Appl. No.: 887,570

[22] Filed: Jul. 21, 1986

[30] Foreign Application Priority Data

Jul. 26, 1985 [FR] France ................... 85 11436

[51] Int. Cl.$^4$ .............................. C07C 69/63
[52] U.S. Cl. .................... 560/226; 560/227; 560/228
[58] Field of Search .................. 560/227, 226

[56] References Cited

U.S. PATENT DOCUMENTS 2,519,983  8/1950  Simons .................. 549/377 X
2,567,011  9/1951  Diesslin et al. ............. 560/227

OTHER PUBLICATIONS

Noller, Chemistry of Organic Compounds, 2nd ed., 1957, pp. 24–25.
Research Disclosure 244,032, Process for Manufacturing Anhydrous Esters of Trifluoroacetic Acid, 10-0-8-84.

Primary Examiner—Donald B. Moyer
Assistant Examiner—Patricia M. Scott
Attorney, Agent, or Firm—Finnegan, Henderson, Farabow, Garrett & Dunner

[57] ABSTRACT

A process for preparing trifluoroacetic or trichloroacetic acid esters, wherein trifluoroacetic or trichloroacetic acid is brought together with a non-perfluorinated alcohol in liquid hydrofluoric acid and wherein the ester obtained is separated by decantation. The trifluoroacetic or trichloroacetic acid esters are used as synthesis intermediates in the pharmaceutical or the plant-protection industry.

9 Claims, No Drawings

PROCESS FOR PREPARING TRIFLUOROACETIC OR TRICHLOROACETIC ACID ESTERS

The present invention relates to a process for preparing trifluoroacetic or trichloroacetic acid esters. It relates more particularly to a process for preparing esters of trifluoroacetic or trichloroacetic acid and non-perfluorinated alcohols.

There are very few processes for esterifying trifluoroacetic acid known in the prior art. For instance, it is known from the publication Research Disclosure No. 244,032 to prepare trifluoroacetic acid esters by a 4-stage process, according to which stages:

an alcohol of the formula ROH, in which R denotes an alkyl radical containing 1 to 5 carbon atoms, is condensed with trifluoroacetic acid in the presence of a strong mineral acid (HCl, $H_2SO_4$ or $H_3PO_4$) at a temperature of 25° to 110° C.;

the mixture obtained is cooled and the aqueous phase removed;

the organic phase is treated with phosphoric acid and/or concentrated sulfuric acid, and the reaction between the acid and the alcohol is then continued at 25°–110° C.; and the ester is isolated by distillation.

This process disadvantageously requires a large number of stages, and the recovery of the anhydrous sulfuric acid is difficult. Sulfuric acid is, furthermore, frequently an excessively oxidizing medium, and this causes reductions in reaction yields.

The present invention has enabled the disadvantages of the prior art to be overcome by providing a process for preparing trifluoroacetic or trichloroacetic acid esters, wherein trifluoroacetic or trichloroacetic acid is reacted with a non-perfluorinated alcohol in liquid hydrofluoric acid and wherein the ester obtained is separated by decantation.

One of the main advantages of the process according to the invention is the fact that no distillation is required at the end of the reaction because a simple decantation suffices, in effect, to separate the ester obtained. Moreover, hydrofluoric acid possesses a viscosity which is much lower than that of sulfuric acid, and this facilitates the technical implementation of the process.

Preferred alcohols which can be used for the esterification are all non-perfluorinated linear or branched alcohols of the formula:

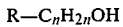

$$R-C_nH_{2n}OH$$

in which n is from 1 to 12, and preferably from 1 to 5. R is chosen from hydrogen or an aromatic substituent.

Illustrative alcohols which can be used include methanol, ethanol, isopropanol, tert-butanol, 2-pentanol and benzyl alcohol.

The hydrofluoric acid used for the esterification is anhydrous or aqueous. When the hydrofluoric acid used is aqueous, it is preferable to used hydrofluoric acid containing at most 60% of water (40% strength hydrofluoric acid).

For the decantation, water is optionally added to the reaction mixture.

For better implementation of the invention, it is preferable to use the alcohol and the trifluoroacetic or trichloroacetic acid in approximately stoichiometric amounts.

It is especially advantageous to use, in particular, an amount of hydrofluoric acid such that the mole ratio of the alcohol or the trifluoroacetic or trichloroacetic acid with respect to the hydrofluoric acid is preferably from 0.1 to 10, and more preferably, from 0.3 to 5.

The reaction temperature is advantageously from 0° to 50° C., and still more advantageously from 10° to 20° C.

The pressure at which the esterification is carried out is preferably atmospheric pressure.

Illustrative products obtained by the process of the present invention include methyl, ethyl, isopropyl and tert-butyl trifluoroacetates.

These products are used as synthesis intermediates in the pharmaceutical or the plant-protection industry (U.S. Pat. No. 4,358,604).

The invention will now be described more completely with the help of the following examples, which in no way limit the invention.

EXAMPLE 1

57 g (0.5 mol) of trifluoroacetic acid, 23 g (0.5 mol) of absolute ethanol and 19 g of 50% strength hydrofluoric acid are introduced successively into a 250-ml polyethylene reactor. After 3 hours stirring at room temperature (approximately 15° C.), the reaction mixture separates into two immiscible phases, which are separated by decantation.

66 g of ethyl trifluoroacetate, equivalent to a 93% yield, are thereby recovered.

EXAMPLE 2

The procedure is identical to that in Example 1, with the following conditions and products:
Trifluoroacetic acid: 57 g (0.5 mol),
2-Pentanol: 44 g (0.5 mol),
Anhydrous hydrofluoric acid: 20 g (1 mol),
Temperature: 10°–15° C.,
Time: 3 hours.

After decantation, 81 g of 2-pentyl trifluoroacetate, equivalent to an 88% yield, are recovered.

EXAMPLE 3

The procedure is identical to that in Example 1, but with the addition of a little water after the reaction, thereby inducing phase separation, and with the following conditions and products:
Trifluoroacetic acid: 57 g (0.5 mol),
Ethanol: 23 g (0.5 mol),
Anhydrous hydrofluoric acid: 20 g (1 mol),
Water: 20 g (1.1 mol),
Temperature: 10° C.
Time: 3 hours 30 min.

After decantation, 66 g of ethyl trifluoroacetate, equivalent to a 93% yield, are recovered.

EXAMPLE 4

The procedure is identical to that in Example 3, with the following conditions and products:
Trifluoroacetic acid: 57 g (0.5 mol),
Methanol: 16 g (0.5 mol),
Anhydrous hydrofluoric acid: 10 g (0.5 mol),
Water: 16 g (0.9 mol),
Temperature: 10°–15° C.
Time: 3 hours.

After decantation, 52 g of methyl trifluoroacetate, equivalent to an 80% yield, are recovered.

EXAMPLE 5

The procedure is identical to that in Example 3, with the following conditions and products:
Trifluoroacetic acid: 57 g (0.5 mol),
Isopropanol: 30 g (0.5 mol),
Anhydrous hydrofluoric acid: 30 g (1.5 mol),
Water: 30 g (1.7 mol),
Temperature: 15° C.,
Time: 3 hours.

After decantation, 74 g of isopropyl trifluoroacetate, equivalent to a 95% yield, are recovered.

EXAMPLE 6

The procedure is identical to that in Example 3, with the following conditions and products:
Trifluoroacetic acid: 57 g (0.5 mol),
Ethanol: 23 g (0.5 mol),
Anhydrous hydrofluoric acid: 5 g (0.25 mol),
Water: 20 g (1.1 mol),
Temperature: 10° C.,
Time: 2 hours 30 min.

After decantation 57 g of ethyl trifluoroacetate, equivalent to an 80% yield, are recovered.

EXAMPLE 7

The procedure is identical to that in Example 3, with the following conditions and products:
Trifluoroacetic acid: 57 g (0.5 mol),
Ethanol: 23 g (0.5 mol),
66% strength hydrofluoric acid: 15 g,
Water: 10 g (0.55 mol),
Temperature: 20° C.,
Time: 3 hours.

After decantation, 64.7 g of ethyl trifluoroacetate, equivalent to an 91% yield, are recovered.

EXAMPLE 8

The procedure is identical to that in Example 3, with the following conditions and products:
Trifluoroacetic acid: 81.5 g (0.5 mol),
Ethanol: 23 g (0.5 mol),
Anhydrous hydrofluoric acid: 5 g (0.25 mol),
Water: 30 g (1.67 mol),
Temperature: 20° C.,
Time: 3 hours.

After decantation, 90 g of ethyl trichloroacetate, equivalent to a 94% yield, are recovered.

EXAMPLE 9

The procedure is identical to that in Example 1, with the following conditions and products:
Trifluoroacetic acid: 57 g (0.5 mol),
Lauryl alcohol: 93 g (0.5 mol),
Anhydrous hydrofluoric acid: 5 g (0.25 mol),
Temperature: 25° C.,
Time: 4 hours 30 min.

After decantation, 118 g of lauryl trifluoroacetate, equivalent to an 83.7% yield, are recovered.

EXAMPLE 10

The procedure is identical to that in Example 1, with the following conditions and products:
Trifluoroacetic acid: 57 g (0.5 mol),
Ethanol: 23 g (0.5 mol),
40% strength hydrofluoric acid: 20 g,
Temperature: 20° C.,
Time: 5 hours 30 min.

After decantation, 55 g of ethyl trifluoroacetate, equivalent to a 77.5% yield, are recovered.

We claim:

1. A process for preparing a trifluoroacetic or trichloroacetic acid ester, comprising the steps of reacting trifluoroacetic or trichloroacetic acid with a non-perfluorinated alcohol in liquid hydrofluoric acid and separating the ester obtained by decantation.

2. The process of claim 1, wherein the non-perfluorinated alcohol, which may be linear or branched, has the formula $$R-C_nH_{2n}OH$$

in which n is from 1 to 12 and R is a hydrogen atom or an aromatic substituent.

3. The process of claim 2, wherein n is from 1 to 5.

4. The process of claim 1, wherein the hydrofluoric acid contains at most 60% of water.

5. The process of claim 1, wherein the mole ratio of the alcohol to the trifluoroacetic or trichloroacetic acid is approximately 1:1.

6. The process of claim 1, wherein the mole ratio of the alcohol or the trifluoroacetic or trichloroacetic acid to the hydrofluoric acid is from about 0.1:1 to 10:1.

7. The process of claim 6, wherein the mole ratio is from 0.3:1 to 5:1.

8. The process of claim 1, wherein the reaction temperature is from 0° to 50° C.

9. The process of claim 8, wherein the reaction temperature is from 10° to 20° C.

* * * * *